United States Patent
You et al.

(10) Patent No.: US 9,308,135 B2
(45) Date of Patent: Apr. 12, 2016

(54) ABSORBENT ARTICLE WITH STABILIZATION MEMBER

(75) Inventors: KueYoung You, Gyunggi-do (KR); HyungWoo Park, Gyeonggi-do (KR); MinJae Lee, Gyeonggi-do (KR); HyungByum Kim, Gyeonggi-do (KR); Karyn C. Schroeder, GyungGi-Do (KR)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 187 days.

(21) Appl. No.: 14/356,683

(22) PCT Filed: Nov. 8, 2011

(86) PCT No.: PCT/US2011/059712
§ 371 (c)(1),
(2), (4) Date: May 7, 2014

(87) PCT Pub. No.: WO2013/070190
PCT Pub. Date: May 16, 2013

(65) Prior Publication Data
US 2014/0316363 A1   Oct. 23, 2014

(51) Int. Cl.
*A61F 13/472* (2006.01)
*A61F 13/47* (2006.01)

(52) U.S. Cl.
CPC ............ *A61F 13/4702* (2013.01); *A61F 13/472* (2013.01)

(58) Field of Classification Search
CPC .......................... A61F 13/4702; A61F 13/472
USPC .................................................... 604/385.31
See application file for complete search history.

(56) References Cited

U.S. PATENT DOCUMENTS

| | | | | |
|---|---|---|---|---|
| 4,828,555 A | * | 5/1989 | Hermansson | A61F 5/4401 604/358 |
| 5,514,104 A | * | 5/1996 | Cole | A61F 5/4401 604/358 |
| 6,007,528 A | | 12/1999 | Osborn, III | |
| 6,198,019 B1 | | 3/2001 | Hansson et al. | |
| 6,231,556 B1 | | 5/2001 | Osborn, III | |
| 6,350,257 B1 | | 2/2002 | Bjoerklund et al. | |
| D455,829 S | | 4/2002 | Drevik et al. | |
| 6,447,494 B1 | | 9/2002 | Kashiwagi et al. | |
| 6,485,477 B2 | * | 11/2002 | Widlund | A61F 13/4702 156/62.6 |
| 6,579,272 B1 | * | 6/2003 | Samuelsson | A61F 13/4702 604/370 |
| 6,740,069 B2 | | 5/2004 | Drevik | |
| 6,866,658 B2 | | 3/2005 | Drevik et al. | |
| 6,929,629 B2 | | 8/2005 | Drevik et al. | |
| 6,945,967 B2 | | 9/2005 | Drevik et al. | |
| 6,953,451 B2 | | 10/2005 | Berba et al. | |
| 7,156,832 B2 | | 1/2007 | Drevik et al. | |

(Continued)

FOREIGN PATENT DOCUMENTS

EP    0 526 225 A1    2/1993
EP    0 335 253 B1    3/1993

(Continued)

*Primary Examiner* — Susan Su
(74) *Attorney, Agent, or Firm* — Kimberly-Clark Worldwide, Inc.

(57) ABSTRACT

The present application discloses and claims an absorbent article which utilizes a stabilizing member within the article having a design which is intended to reduce the amount of vertical bunching of the product when the product is subjected to lateral compressive forces as are commonly exerted by a wearer during use of the article.

18 Claims, 7 Drawing Sheets

(56) References Cited

U.S. PATENT DOCUMENTS

| | | | |
|---|---|---|---|
| 7,166,093 B2 * | 1/2007 | Drevik | A61F 13/47272 604/385.01 |
| 7,316,673 B2 * | 1/2008 | Drevik | A61F 13/4702 604/358 |
| 7,601,144 B2 * | 10/2009 | Drevik | A61F 13/4702 604/378 |
| 8,048,052 B2 * | 11/2011 | Kurihara | A61F 13/4704 604/385.01 |
| 8,153,856 B2 * | 4/2012 | Wallstrom | A61F 13/47218 604/358 |
| D701,367 S * | 3/2014 | Wexler | D2/712 |
| 8,877,999 B2 * | 11/2014 | Carbonari | A61F 13/49001 604/378 |
| D724,819 S * | 3/2015 | Wexler | D2/712 |
| 9,192,524 B2 * | 11/2015 | Orchard, IV | A61F 13/49006 |
| 2001/0039407 A1 * | 11/2001 | Widlund | A61F 13/4702 604/385.01 |
| 2007/0135788 A1 | 6/2007 | Damay et al. | |
| 2009/0292268 A1 | 11/2009 | Bagger-Sjoebaeck et al. | |

FOREIGN PATENT DOCUMENTS

| | | |
|---|---|---|
| EP | 0 637 952 B1 | 10/1996 |
| EP | 0 335 252 B1 | 12/2001 |
| EP | 0 771 182 B1 | 12/2001 |
| EP | 1 349 525 B1 | 4/2005 |
| EP | 1 022 009 B1 | 1/2008 |
| WO | WO 94/09737 A1 | 5/1994 |
| WO | WO 95/07674 A2 | 3/1995 |
| WO | WO 95/31165 A1 | 11/1995 |
| WO | WO 96/12460 A1 | 5/1996 |
| WO | WO 97/09015 A1 | 3/1997 |
| WO | WO 98/17218 A1 | 4/1998 |
| WO | WO 02/47594 A1 | 6/2002 |
| WO | WO 02/085269 A1 | 10/2002 |
| WO | WO 02/085270 A1 | 10/2002 |
| WO | WO 02/087483 A1 | 11/2002 |
| WO | WO 02/087484 A1 | 11/2002 |
| WO | WO 03/047484 A1 | 6/2003 |
| WO | WO 03/053301 A1 | 7/2003 |
| WO | WO 03/059222 A1 | 7/2003 |
| WO | WO 2005/063160 A1 | 7/2005 |

* cited by examiner

ABSORBENT ARTICLE WITH STABILIZATION MEMBER

BACKGROUND OF THE INVENTION

The present invention is directed to absorbent articles and in particular personal care absorbent articles utilized to collect and retain body fluids or exudates including, but not limited to, urine, feces and menses. In the context of such products, wearer comfort and absorbency are two main attributes and areas of concern for the wearer. This is particularly true with feminine care products such as sanitary napkins, panty liners and incontinence products.

A common problem with absorbent articles such as sanitary napkins is their tendency to bunch and ride up into the contours of the body including the buttocks and the vagina during use. This is a common complaint amongst users resulting in overall dissatisfaction with the product despite its absorbency capabilities. Most absorbent articles are relatively planar in design prior to being worn, planar being defined as the X-Y plane of the product corresponding to the longitudinal and transverse axes of the product. When placed into the crotch area of a wearer's undergarment, as the products are designed to do, they take on a relatively curved shape in the longitudinal direction (from the front to the back of the undergarment) but it is still desired that the product remain relatively flat and planar in the transverse or lateral direction to maintain wide coverage and permit the product to trap and retain body fluids such as urine and menses. To overcome this problem, a number of designs have been proposed which employ layers and/or overall designs in which there are areas of the layers and/or overall product design where material has been removed. See, for example, U.S. Pat. No. 5,514,104 which discloses absorbent articles with one or more V-shaped notches cut at both ends of the pad to supposedly provide an ergonomic fit and to reduce stiffness. U.S. Publication No. 2007/0135788 A1 discloses a panty liner with end notches and side notches located in the product. U.S. Publication No. 2005/0124953 discloses an absorbent article with segmented absorbent pads which are transversely separated by a flexible zone. The flexible zone is said to be minimally absorbent and preferentially deforms before the segmented absorbent pad. Lateral force on the absorbent article compresses the flexible zone and reduces the transverse width of the absorbent article. WO 2008/004961 discloses an absorbent article with a core that has a first region comprising two legs which extend in the longitudinal direction of the article over at least parts of the crotch portion of the article towards the rear portion with a maximum facing distance between the legs in the crotch portion. U.S. Pat. No. 6,740,069 discloses an absorbent article wherein one layer of the absorbent core is split into a first leg and a second leg. WO 2003/059222 discloses an absorbent article which has a second stiffening part element which is arranged in the rear portion of the article and extends part of the way over the crotch portion. The second stiffening part element has a cutout extending from its end edge in the direction towards the crotch portion as a result of which the stiffening element forms legs which are located on both sides of the cutout and are more flexible than the rest of the second part element.

Despite these design attempts, there is still a need for a product which when worn, resists the tendency to bunch or ride up in the vertical or Z-direction of the product relative to the X-Y plane of the product. To reduce this problem, the present invention employs a stabilizing member which allows the product to stay in a more planar configuration, especially in the front and/or rear portions of the product.

SUMMARY OF THE INVENTION

Objects and advantages of the invention are set forth below in the following description, or may be obvious from the description, or may be learned through practice of the invention.

In one embodiment of the invention, an absorbent article includes a front end portion having a front end, a rear end portion having a rear end and a central portion separating the front end portion and the rear end portion. The article includes a liquid permeable body-side layer and a garment-side layer with an absorbent core positioned between the body-side layer and the garment-side layer of the article. The article further includes a stabilizing member positioned between the body-side layer and the garment-side layer of the article with the stabilizing member being made from a stabilizing material and including a pair of lobes located in at least one of the front end portion or the rear end portion of the article. The pair of lobes extends away from the central portion towards a respective front or rear end of the article with the pair of lobes defining a void therebetween which is devoid of the stabilizing member material. The void so defined by the pair of lobes is generally centered about a lengthwise centerline of the article with each of the lobes in the pair having a proximal end adjacent the central portion and a distal end separated by a mid-section. The distal ends of each of the lobes are separated by a distal distance, the proximal ends of each of the lobes are separated by a proximal distance and the mid-section of each of the lobes is separated by a mid-distance. The distal distance between each of the lobes in a pair is greater than the proximal distance and the mid-distance is less than the proximal distance. Further, the void defined by the pair of lobes does not extend into the central portion of the article.

In another embodiment, the absorbent article may have a pair of lobes located in both the front end portion and the rear end portion of the article. The shapes of each of the pairs of lobes may be the same or different than the other pair of lobes and the proximal, mid-section and distal distances of one pair of lobes may each be the same or different than those of the other pair of lobes.

In an alternate embodiment of the present invention, the article may have at least one embossment which extends over the stabilizing member and at least a portion of the void defined by the stabilizing member. The embossment may be in multiple layers of the absorbent article as well.

The portion of the lobes adjacent the proximal end may terminate in a shape which causes the void to be defined by a relative V-shape about the lengthwise centerline of the absorbent article with an open end of the V-shape pointing towards the central portion of the absorbent article. In other embodiments independent of the foregoing and independent as to each other, the stabilizing member may define a void area with a substantially rounded end adjacent the central region or a substantially triangular end adjacent the central region or a diamond-shaped end adjacent the central region.

The absorbent core of the absorbent article can comprise a fibrous nonwoven web material including at least 80% by weight viscose rayon and in alternate embodiments this web material can comprise a hydro entangled viscose rayon spun lace material.

In yet other embodiments of the present invention, the stabilizing member can comprise, among other materials, a foam material, a through air bonded cared web or a chemically-bonded carded web.

In separate embodiments of the present invention, the absorbent article may have a proximal distance of between about 10 and about 40 millimeters. Independently or in combination therewith, the article may have a mid-distance of between about 1 and about 30 millimeters. Independently or in combination therewith, the article may have a distal distance between about 30 and about 70 millimeters.

In still further embodiments of the present invention, the absorbent article may have a stabilizing member with a length which is between about 80 and about 120 percent of the length of the absorbent core. Independently or in combination therewith, the article may have a stabilizing member with a width which is between about 70 and about 140 percent of the width of the absorbent core. Independently or in combination therewith, the article may have a stabilizing member with a basis weight between about 40 and about 120 grams per square meter.

Those of ordinary skill in the art will better appreciate the features and aspects of such embodiments, and others, upon review of the specification.

BRIEF DESCRIPTION OF THE DRAWINGS

A full and enabling disclosure of the present invention is set forth more particularly in the remainder of the specification, including reference to the accompanying figures, in which.

DETAILED DESCRIPTION OF PREFERRED EMBODIMENTS

Reference will now be made in detail to present embodiments of the invention, one or more examples of which are illustrated in the accompanying drawings. Each example is provided by way of explanation of the invention and not a limitation of the invention. In fact, it will be apparent that modifications and variations can be made in the present invention without departing from the scope or spirit thereof. For instance, features illustrated or described as part of one embodiment may be used on another embodiment to yield a still further embodiment. Thus, it is intended that the present invention covers these and other such modifications and variations as come within the scope of the appended claims and their equivalents.

The present invention relates generally to an absorbent article 10 for intercepting and retaining body fluids or exudates. The accompanying figures depict the absorbent article 10 as a sanitary napkin for feminine hygiene having a elongated shape with generally rounded ends; however, the absorbent article 10 may also be a panty liner, shield, diaper, training pant, adult incontinent garment, or any other disposable absorbent article known in the art including bandages. Moreover, the 5 absorbent article 10 may have other shapes, such as hourglass or rectangular shapes, and varying sizes and thickness, depending on the particular application.

Figure 1:
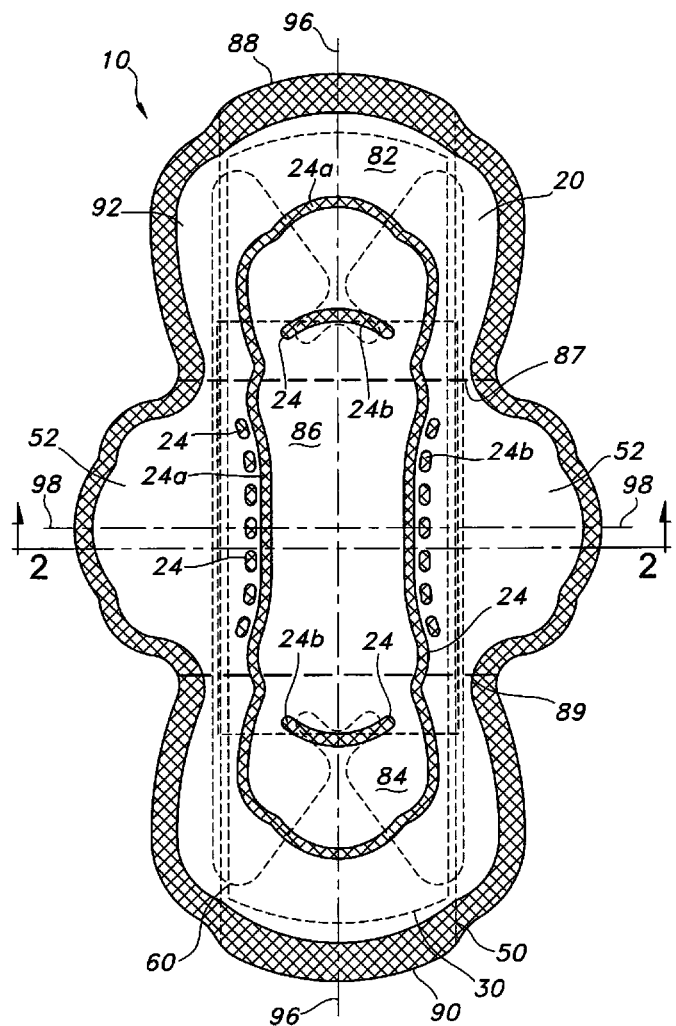
FIGS. 1 and 1A are top plan views of embodiments of the present invention.
Figure 2:
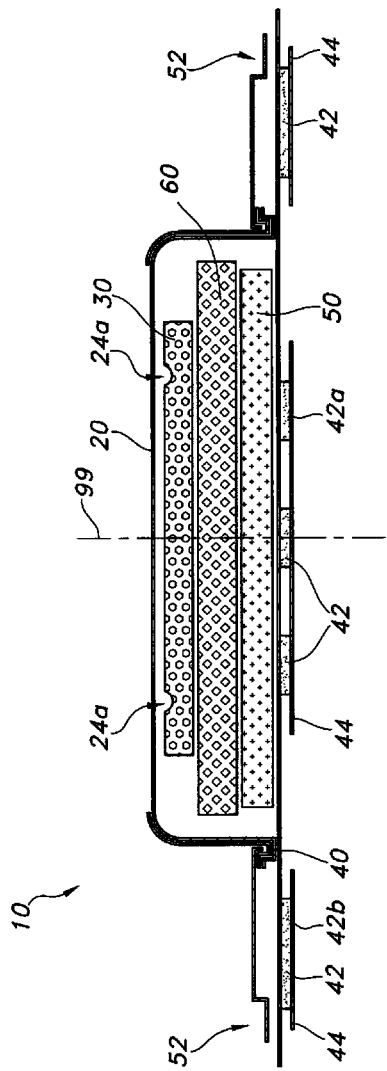
FIG. 2 is a cross-sectional side view of the present invention taken along line 2-2 of FIG. 1.
Figure 3:
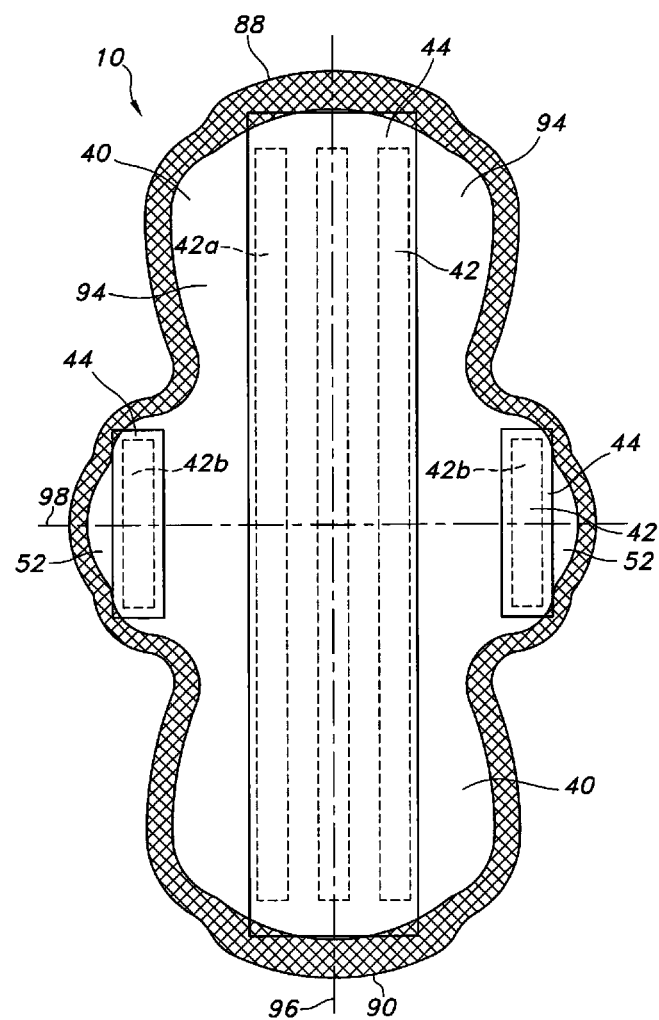
FIG. 3 is a bottom plan view of an embodiment of the present invention.
Figure 4:
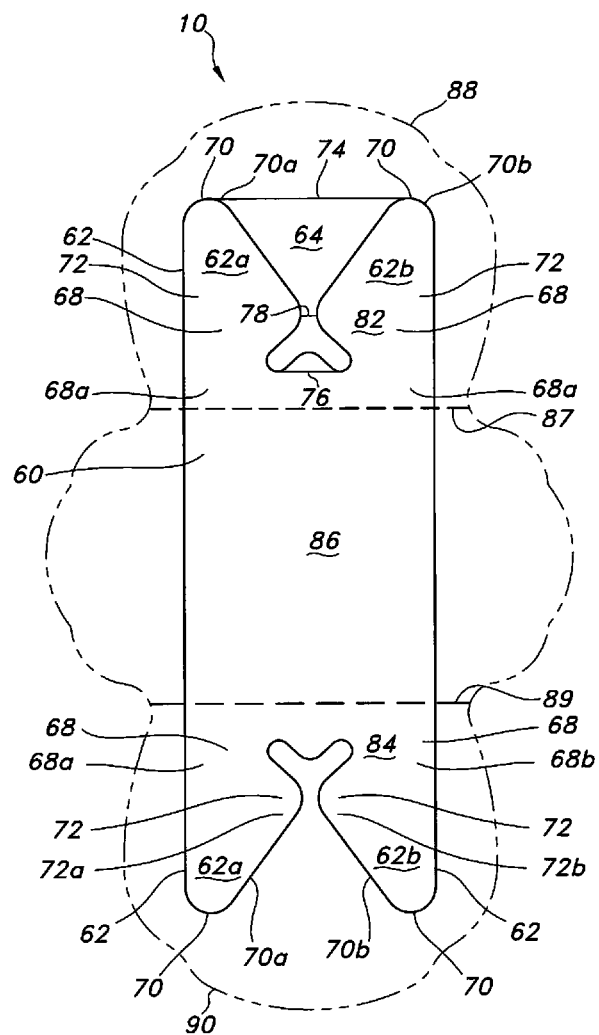
FIGS. 4 and 5 are a top plan view of a stabilizing member of the present invention.

Referring to FIGS. 1, 2 and 3, the absorbent article 10 generally includes a top sheet, body side layer or cover 20, an optional transfer or surge layer 30, a back sheet, garment-side layer or baffle 40, and an absorbent core 50.

The top sheet or cover or body-side layer 20 provides the absorbent article 10 with a liquid permeable surface that contacts the user's skin. The body side layer 20 should provide a comfortable, conforming interface with the user's skin by being flexible, compliant, and non-irritating to the skin. The body side layer 20 should also transfer fluids quickly to underlying layers and remain dry and clean during use. In addition to being liquid permeable, the body side layer 20 may also include apertures (not shown) for freely passing exudates with minimal absorption. The body side layer 20 may be coated with a surfactant to further enhance permeability to the absorbent core 50 and reduce retention of fluids by the body side layer 20. The body side layer 20 may also include embossments 24 such as embossed channels 24a and arcuate embossments 24b to create an aesthetically pleasing surface and further disperse exudates passing through the body side layer 20. Furthermore, if so desired, these embossments 24 may extend down into one or more other layers of the product to enhance the fluid handling properties of the product and may serve to attach the body side layer 20 to subjacent layers.

The body side layer 20 may be any woven or non-woven material which passes body fluids yet remains comfortable to the user. Suitable nonwoven materials include, but are not limited to, spunbond webs and bonded carded webs made from staple fibers. Apertured films are also suitable cover materials. Examples of suitable cover materials include rayon, polyester, polyolefins including polypropylene and polyethylene, copolymers of polypropylene and polyethylene, linear low-density polyethylene, nylon, or other heat-bondable fibers, and aliphatic esters such as polylactic acid.

One example of a suitable bonded carded web cover material is a through-air bonded carded webs (TABCW) made from staple length fibers generally ranging in length from 25 to 50 millimeter (mm). If desired, the TABCW, as with other suitable fibrous webs, may be mechanically perforated to increase fluid intake and/or embossed to increase fluid handling properties.

Another example of such a TABCW material is a 25 gram per square meter (gsm) web made with 1.5 denier (d), polyethylene sheath, polypropylene core bicomponent staple fibers having a staple length of approximately 35 mm available from FiberVisions Corporation with offices in Duluth, Ga., USA. These fibers are available under the trade designation ESC215.

In addition, the cover material may be a multi-component material with a central section (not shown) running along and straddling the longitudinal centerline of the product with lateral side sections (not shown) flanking and joined to either side of the central section. The central section may be made from the aforementioned TABCW materials as well as other nonwovens or it may be made from a perforated film. The lateral side sections may be made from a different fibrous nonwoven material or film which is joined to the central section. Other examples of such cover materials can be found in U.S. Pat. Nos. 5,533,991 and 5,415,640 to Kirby et al. and U.S. Pat. No. 5,961,505 to Coe et al. which are each incorporated herein by reference in their entirety to the extent they do not conflict herewith.

The surge or transfer layer 30 provides an optional layer between the body side layer 20 and the absorbent core 50. When present, the transfer layer 30 wicks fluid passing through the body side layer 20 and disperses the fluid to subjacent layers including the absorbent core 50. The transfer layer 30 may comprise any of the fibers, polymers and fibrous and film structures mentioned above with respect to the cover material as well as any surge materials as are readily available and known to those of ordinary skill in the art of fibrous nonwoven webs, films and personal care absorbent articles.

One example of a surge or transfer layer 30 is a fibrous, single layer nonwoven web available from the Sambo Company, LTD located in Daegu, Korea. Such webs can have basis weights ranging from 20 to 40 gsm. This specific web was a 25 gsm TABCW made from a blend of 80% by weight ESC-UB HR6 polyethylene sheath/polypropylene core bicomponent 5 denier (d) staple fibers having a 35-40 mm fiber length (available from the aforementioned FiberVisions Corporation) and 20% by weight polyester (PET) 3d staple fibers having a fiber length of 35-40 mm which are available from the Huvis Company, LTD of Seoul, Korea and sold under the trade designation SD-10.

No matter which surge layer material is being used, the surge or transfer layer can run the full length of the product or it may be shorter and strategically located in a specific area of the product. In addition, it can be a full width layer extending to the lateral sides of the product or it may have a shorter width in which case it will generally be centered on the longitudinal centerline 96 of the product.

The back sheet, or garment-side layer or baffle 40 may be peripherally joined to the body side layer 20, usually about the periphery of the product, either directly or indirectly through intermediate layers. It provides the absorbent article 10 with a liquid impermeable and optionally vapor permeable surface that prevents exudates from completely penetrating the absorbent article 10 and soiling the user's undergarment. Ideally, the garment side layer 40 is soft, flexible, quiet, breathable, and may include some absorbent capacity on the side facing the absorbent core 50.

Referring to FIG. 3, the exterior surface of the garment side layer 40 may include adhesive strips or other suitable fastening device 42 (42a and 42b) for adhering the absorbent article 10 to the user's undergarment. Prior to use, the adhesive strips 42a on the main body of the article 10 are covered by a peel strip 44 which is removed to expose the adhesive strips for subsequent attachment to the inner or outer surfaces of the wearer's undergarment. The garment side layer 40 may be any suitable material known in the art, such as embossed and non-embossed thermoplastic films, nonwoven webs, laminated tissue, and combinations of the foregoing. In one embodiment, the garment side layer 40 includes a non-woven material laminated to a microporous film with the nonwoven material forming a soft and comfortable exterior surface to the absorbent article 10. Alternatively, the garment side layer 40 may comprise a breathable polyethylene (PE) film. Typically such films will have a thickness of about 0.03 to about 0.07 mm though other thicknesses may be used depending upon the particular end use of the product. Such films also may be breathable and have water vapor transmission rates (WVTR) of 500 to 2500 grams per square meter per day though other transmission rates may be used depending upon the particular end use of the product.

One example of a film suitable for use as the garment side layer 40 is one comprising 50% by weight calcium carbonate and 50% by weight PE as is available from DaeMyung Chemical Company, LTD located in MunGyong-City, Kyung-Bok, Korea. It has a thickness of 0.05 mm, a basis weight of 35 gsm and a WVTR of 500 grams per square meter per day.

The absorbent core 50 provides the operative material for collecting and retaining body fluids or exudates while remaining light and dry feeling during use. It is desirable that the absorbent core 50 be soft and retain its shape, even when wet. The absorbent core 50 resides between the body side layer 20 and garment side layer 40 and may be attached to either or both layers or to intermediate layers such as the optional surge layer 30 to hold the absorbent core 50 in place and protect the absorbent core 50 from abrasion. The absorbent core 50 is typically about 2 to about 10 millimeters thick but thicknesses outside this range are also permissible depending on the particular application.

The absorbent core 50 may be any structure or combination of components which are generally compressible, conformable, non-irritating to the user's skin, and capable of absorbing and retaining bodily fluids. For example, the absorbent core 50 may include an absorbent web of cellulose fibers, such as wood pulp fibers, other natural fibers, synthetic fibers, woven or non-woven sheets, scrim netting or other stabilizing structures, superabsorbent materials, binder materials, surfactants, selected hydrophobic and hydrophilic materials, pigments, lotions, and odor control agents, as well as combinations thereof. In one embodiment, the absorbent core 50 is a matrix of cellulose fluff with superabsorbent hydrogel-forming particles. The absorbent core 50 may be formed using various methods and techniques known in the art, such as dry-forming, air forming, wet-forming, and foam-forming, as well as combinations thereof.

Superabsorbent materials are well known in the art and may be selected from natural, synthetic, and modified natural polymers and materials. The absorbent core 50 generally includes superabsorbent material, with the superabsorbent material ranging from about 1-90 percent by weight of the absorbent core 50, depending on the application and desired absorbency. For example, the total absorbency may be about 200-900 grams of 0.9% by weight saline solution for infant care products; whereas, the total absorbency for adult care products may be about 400-2000 grams of 0.9% by weight saline solution. For feminine care products, the total absorbency may be within the range of about 7-50 grams of menstrual fluid. Optionally, the absorbent core 50 may include what is termed a core wrap (not shown) made from tissue or a nonwoven such as a spundbond or a meltblown nonwoven or a laminate of spunbond and meltblown layers, the purpose of which is to aid in retaining the superabsorbent particles within the absorbent core 50 and increasing both the wet and dry strength and integrity of the absorbent core 50.

A material that has been found to work particularly well as an absorbent core 50 is a spunlace material, especially materials containing at least 80% by weight viscose rayon. One such material is a hydroentangled viscous rayon spunlace web having a basis weight of 100 gsm which is made completely from 1.7 decitex viscous rayon, 40 mm long staple fibers. The fibers themselves are manufactured by Lenzing Aktlengesellschaft in Lenzing, Austria and are sold under the trade designation Viscose Rayon 55. The spunlace web itself is available from BaikSan Company, LTD located in Kyunggi-do, Korea.

Such spunlace layers can be adhesively attached to the stabilizing member 60 using adhesives either alone or in combination with other bonding techniques such as embossing using heat and/or pressure or ultrasonics.

Referring again to FIGS. 1 and 3, the absorbent article may optionally include what are termed a pair of wings or flaps 52 extending laterally from the central portion of the product. Such wings or flaps 52 are well known in the art and may be integrally formed from other components of the article such as the body side layer 20 and garment side layer 40 or from separate materials and then attached to the sides of the product. They too are fitted with adhesives 42b and peel strips 44. The purpose of such wings is to further secure the absorbent article to the undergarment of the wearer by folding the wings to the underside or exterior of the undergarment and attaching the wings to the exterior surface of the undergarment or to themselves using garment adhesives in the same general manner as the garment adhesives 42b used on the main body of the absorbent article 10.

The various layers of the absorbent article 10 may be joined or not joined to one another depending on the design criteria of the specific product. In this regard, any conventional joining techniques may be used including, but not limited to, adhesives, bonding and embossing techniques using heat and/or pressure, ultrasonic bonding, needling, hyrdoentangling, etc. In most instances it is desirable to seal one or more layers together about the periphery of the product so as to reduce leakage of absorbed body fluids.

Figure 1A:
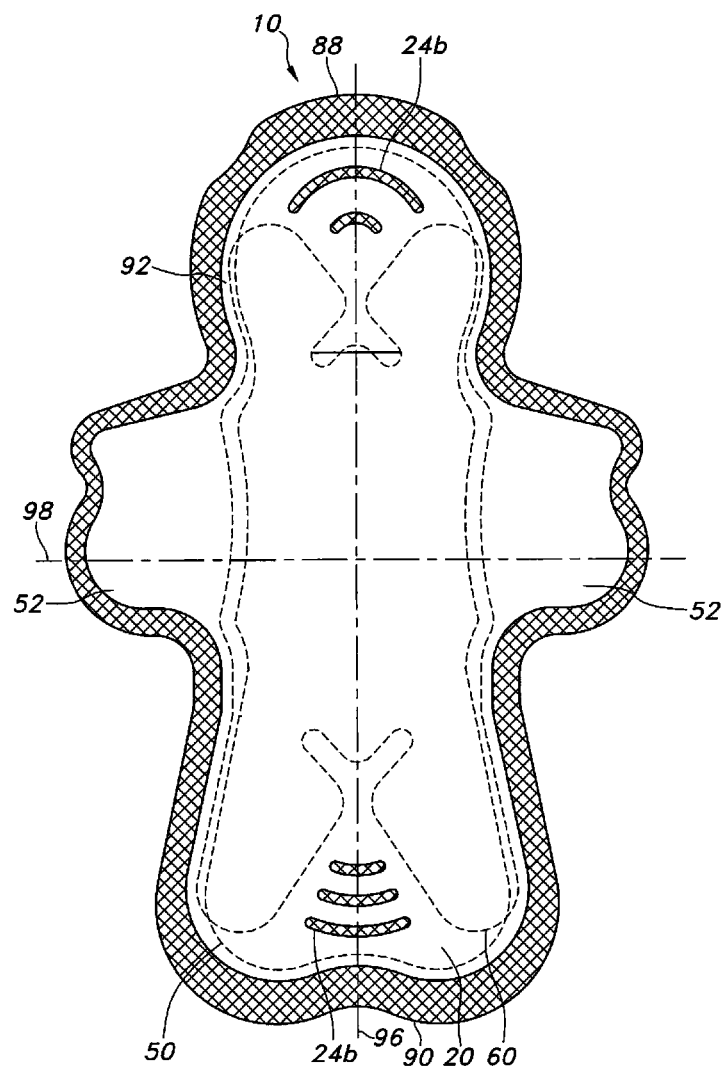

Referring again to FIGS. 1 and 1A and in particular FIGS. 4, 5 and 5A through 5D, the absorbent article 10 contains a stabilizing member 60 for controlling the contour and bunching of the product during use. A common problem with absorbent articles such as sanitary napkins is their tendency to bunch and ride up into the contours of the body including the buttocks and the vagina during use. This is a common complaint amongst users resulting in overall dissatisfaction with the product despite its absorbency capabilities. Most absorbent articles are relatively planar in design prior to being worn in what is termed the X-Y plane of the product. When placed into the crotch area of a wearer's undergarment, as the products are designed to do, they take on a relatively curved shape in the longitudinal direction (from the front to the back of the undergarment) but it is still desired that the product remain relatively flat and planar in the lateral direction to maintain wide coverage and permit the product to trap and retain body fluids such as urine and menses. To reduce this problem, the present invention employs a unique stabilizing member 60 which allows the product to stay in a more planar configuration, especially in the front and rear ends of the product. As a result, the product tends to resist the tendency to bunch up and deflect in the vertical direction along the Z axis of the product which is perpendicular to the plane of the product formed by the X and Y axes. As shown in the drawings, this stabilizing member 60 is located above the absorbent core 50 more adjacent the body side layer 20, however, it is also possible to locate it below the absorbent core 50 more adjacent the garment side layer 40. Once again, it should be noted that the surge layer 30 is optional.

To understand the special aspects of the product as a whole and the stabilizing member 60 in particular, the absorbent article 10 can be defined as having front end portion 82 having a front end or edge 88, a rear end portion 84 having a rear end or edge 90 and a central portion 86 separating the front end portion 82 and rear end portion 84. The article further has a first side or surface 92 typically referred to as the body facing side and a second side or surface 94 typically referred to as the garment-facing side or surface 94. In addition, the article has a longitudinal or lengthwise centerline or X axis 96 and a lateral or transverse centerline or Y axis 98. The Z axis 99 is perpendicular to the plane formed by the X and Y axes as shown in FIG. 2.

The central portion 86 is located in the mid-section of the product and is the area of the product most likely to receive body exudates. It is desirable that the central portion 86 be defined as the approximate middle one-third of the overall length of 5 the product as measured in the longitudinal direction from the front end or edge 88 to the rear end or edge 90. In FIG. 1, the central portion 86 is demarcated by the dashed lines 87 and 89. The central portion is defined as to not include the hereinafter defined lobes 62 or void area 64 of the stabilizing member 60. The lowermost termination point of the lobes 62 is defined by drawing a line 85 tangent to the bottommost portion of the void area 64 closest to the lateral centerline 98 with the tangent line so drawn being parallel to the lateral centerline 98. (See FIGS. 5 and 5C.) Thus, when drawing the dashed lines 87 and 89, they should be located at a point which does not encompass these lobes 62 and voids 64 within the portion of the product defining the central portion 86. At a minimum, however, the central portion 86 should include an area of the overall absorbent article 10 that includes the lateral centerline 98 of the product 10 and at least 20% of the maximum length of the absorbent article 10 (from front edge 88 to rear edge 90) as measured in the longitudinal direction of the article 10. Thus, the central portion 86 will, at a minimum, include 20% of the overall length of the product and generally will extend laterally towards the sides of the absorbent article 10. The remainder of the length of the product can be divided between the front end portion 82 and the rear end portion 84. In some embodiments, the central portion 86 is generally centered on the lateral centerline 98 of the product and the front and rear end portions 82 and 84 equally divide the remaining length of the product such as is shown in FIG. 1. It is also possible to skew the dimensions of the three portions (front, central and rear) to meet particular design parameters or desires. For example, asymmetric pads are widely available in which the size and length of the rear end portion 84 is greater than the front end portion 82. See FIG. 1A. As a result, it is also possible to shift the central portion 86 off of the lateral centerline 98 more towards the front or rear end portions of the product and to change the overall size of the central portion 86 relative to either or both of the front end portion 82 and the rear end portion 84.

Turning again to FIGS. 1, 4 and 5, the stabilizing member 60 has a pair of laterally opposed lobes 62 (62a and 62b) which can be located in at least one or both of the front end portion 82 and the rear end portion 84 of the article 10. As shown in the Figures, there is a pair of lobes 62 located in both the front and the rear end portions 82 and 84 respectively. The lobes 62a and 62b extend away from the central portion 86 of the article 10 toward a respective front end 88 or rear end 90 of the product. The lobes 62a and 62b define a void 64 therebetween due to the removal of material from the stabilizing member 60 or due to the formation of the lobes 62 from separate pieces of material that are then joined together, typically in an area adjacent the longitudinal centerline 986 of the product. Alternatively, the void 64 and the lobes 62a and 62b may be formed as a result of the stabilizing member 60 being formed in a mold having the desired end shape as when using pockets in a forming drum in connection with fibrous structures or a shaped mold when using foam materials. This void area 64 is generally centered about the lengthwise centerline 96 of the overall article 10. Each of the lobes 62 has a proximal end 68 (68a and 68b) adjacent the central portion 86 and a distal end 70 (70a and 70b) adjacent the respective front edge 88 and rear edge 90 of the product. The proximal 68 and distal 70 ends of the lobes 60 (60a and 60b) are separated by a mid-section 72 (72a and 72b). The void 64 created by the respective shapes of the lobes allows the pad to resist bunching and movement of the product in the vertical or Z-direction 99 of the article 10 in the portions of the article containing the lobes and voids thereby making the article more comfortable to wear. The distal ends 70 (70a and 70b) of the lobes 62 (62a and 62b) are separated by a distal distance 74, the proximal ends 68 (68a and 68b) of the lobes 62 are separated by a proximal distance 76 and the mid-section 72 (72a and 72b) of the lobes 62 is separated by a mid-distance 78. The distal distance 74 is greater than the proximal distance 76 and the mid-distance 78 is less than the proximal distance 76.

Figure 5:
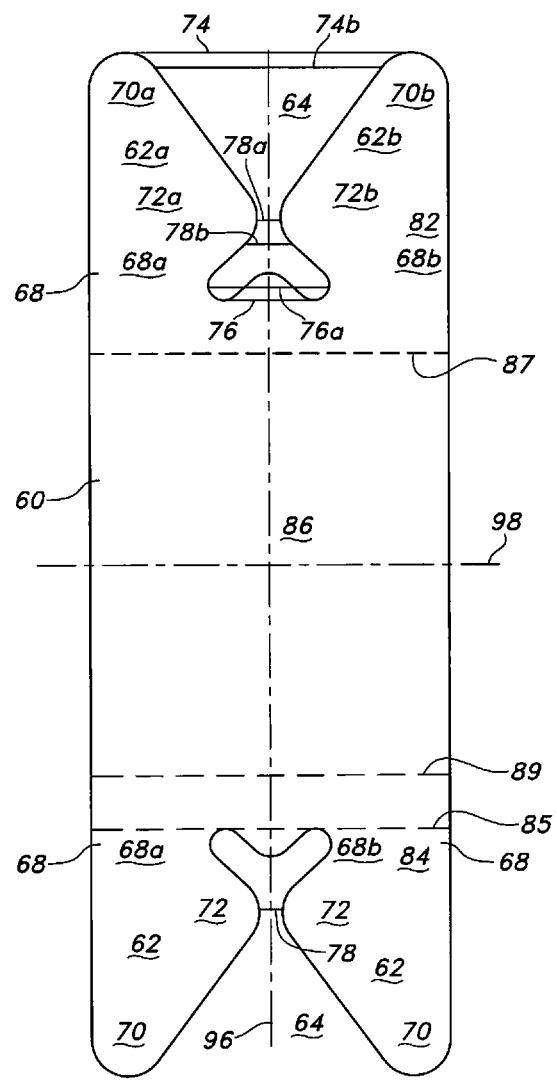
Figures 5A, 5B:
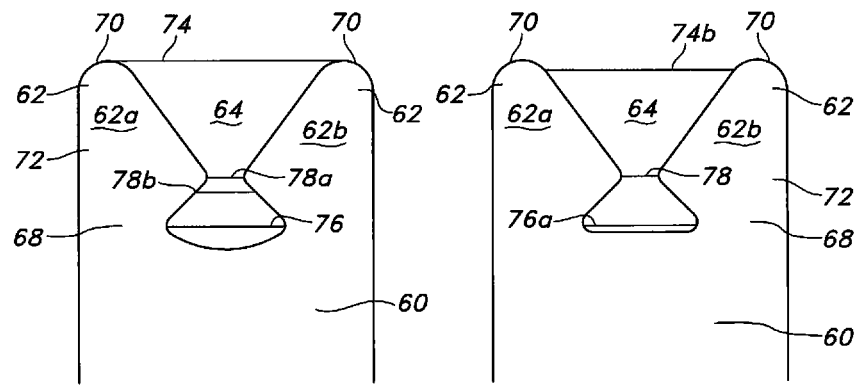
FIGS. 5A, 5B, 5C and 5D are partial top plan views of alternate stabilizing members according to the present invention.
Figures 5C, 5D:
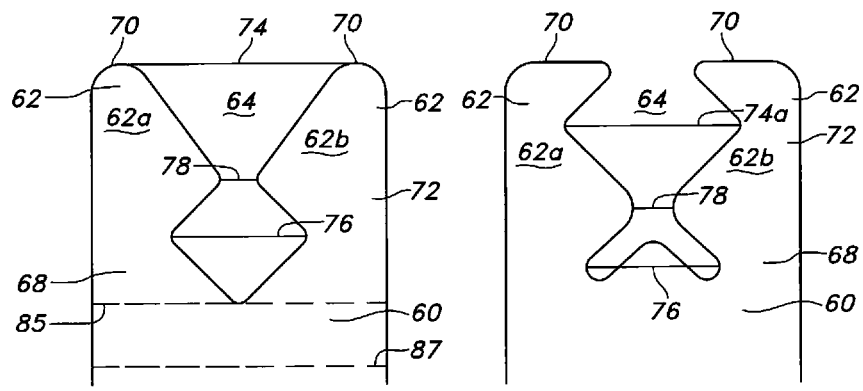

The design of the lobes 62 and the resultant void 64 therebetween can take multiple shapes provided the proximal 76, mid 78 and distal 74 distances meet the parameters set forth above. The distal distance 74 is generally the widest distance between the two lobes, is located adjacent or in the area of the lobes 62 closer to the distal end 70 of the stabilizing member 60 and therefore defines the widest part of the void 64. As shown in FIG. 5 the distal distance is measured along a line 74 which in this case is tangent to the distal end 70 of each of the lobes 62 in the stabilizing member 60. In FIG. 5D, the lobes 62 are shown with a different shape but they still include the relative distances set forth above with respect to the proximal, mid and distal distances. As shown in FIG. 5D, the widest distance between the two lobes 62a and 62b is not directly at the end of the lobes 62 but instead inboard of the ends as shown by the line/distal distance 74a.

Intermediate the proximal 68 and distal 70 ends of the lobes 62, the lobes 62 must be separated by a mid-distance 78 which is less than the proximal distance 76 and thus, less than a distal distance 74. Accordingly, it can be seen that these lines and resultant distances can be drawn at more than one location to satisfy the spatial relationship defining the invention. As can be seen in FIG. 5A, the mid-section line and distance 78 can be drawn at several points (78a and 78b) between lobes 62a and 62b which still meet the requirement that the mid-distance 78 be less than the proximal distance 76. The same is also true with respect to where the lines are drawn for the proximal and distal distances, 76 and 74 respectively. See elements 76a and 74b in FIGS. 5 and 5B.

The proximal distance 76 is a distance located beyond the mid-distance 78 and closer to the central portion 86 of the article 10 than the mid-distance 78. As stated above, it too can be drawn at multiple locations provided it meets the spatial relationship that the distance chosen is greater than a mid-section distance 78 due to the shape of the lobes 62. For example, in FIG. 5, the proximal distance and line can be drawn at reference point 76 or 76a and still satisfy the spatial requirements of this present invention. Proximal distance 76a is shown being drawn just inboard of the lowest-most portion of the void area 64 and it also crosses a portion of the stabilizing member material 60 while proximal distance 76 is drawn tangent to the proximal ends 68 (68a and 68b) of the lobes 62 (62a and 62b).

In FIGS. 1, 1A, 4, 5 and 5D, the lobes 62 adjacent their proximal ends 68 are 5 shaped in such a way as to form a relative V-shape to the void area 64 generally located about the lengthwise centerline 96 of the absorbent article 10. As shown, because the lobes 62 terminate in this V-shape, the open end of the V points towards the central portion 86 of the article 10 and thus forms hinge points thereby allowing the distal ends 70 of the lobes 62 to rotate inwardly towards the longitudinal centerline 96 of the absorbent article 10 when the article is subjected to lateral compressive forces by the wearer of the product.

As shown in FIGS. 5A, 5B and 5C, the lobes 62 can take on other shapes and still satisfy the requirements of the present invention. For example, in FIG. 5A, the proximal ends 68 of the lobes 62 are shaped such as to define a void area 64 adjacent the proximal ends 68 of the lobes that is more rounded in shape than is shown in FIG. 5. In FIG. 5B, the lobes 62 are shaped such that the void area 64 is more triangular in shape with a relatively flat bottom end and in FIG. 5C, the void area 64 is more of a diamond shape. Note, however, that in each embodiment the requirements that there be a distal distance 74 that is greater than a proximal distance 76 and that there be a mid-distance 78 that is less than a proximal distance 76 are met.

In the context of absorbent articles including feminine hygiene products such as sanitary napkins and panty liners, it is desirable that the proximal distance 76 be between about 10 and about 40 millimeters. More desirably, the proximal distance 76 is between about 15 and about 30 millimeters.

In the context of absorbent articles including feminine hygiene products such as sanitary napkins and panty liners, it is desirable that the mid-distance 78 be between about 1 and about 30 millimeters. More desirably, the mid-distance 78 is between about 3 and about 15 millimeters.

In the context of absorbent articles including feminine hygiene products such as sanitary napkins and panty liners, it is desirable that the distal distance 74 be between about 30 and about 70 millimeters. More desirably, the distal distance 74 is between about 40 and about 60 millimeters.

As to overall length, in the context of absorbent articles including feminine hygiene products such as sanitary napkins and panty liners, the stabilizing member 60 should generally approximate the size of the absorbent core 50 though it may be larger or smaller than the absorbent core if so desired. Generally, it is desirable that the stabilizing member 60 length be between about 80 and about 120 percent of the length of the absorbent core 50. More desirably, the overall length of the stabilizing member 60 will be between about 90 and about 110 percent of the length of the absorbent core 50. In making this calculation, the maximum length parallel to the longitudinal axis 96 of each of the materials should be used.

As to overall width, in the context of absorbent articles including feminine hygiene products such as sanitary napkins and panty liners, the stabilizing member 60 should generally approximate the size of the absorbent core 50 though it may be larger or smaller than the absorbent core if so desired. Generally, it is desirable that the stabilizing member 60 will have a width of between about 70 and about 140 percent of the width of the absorbent core 50. More desirably, the overall width of the stabilizing member 60 will be between about 90 and about 120 percent of the width of the absorbent core 50. In making this calculation, the maximum width parallel to the transverse axis 98 of each of the materials should be used.

As to basis weight, the stabilizing member 60 can have any basis weight that is commensurate with the particular end use. In the context of absorbent articles including feminine hygiene products such as sanitary napkins and panty liners, basis weights between about 40 and about 120 grams per square meter are desirable and more desirably between about 60 and about 100 grams per square meter. In addition, the basis weights in each of the front end portion 82, the rear end portion 84 and the central portion 86 of the stabilizing member 60 may be varied with respect to one another. Further, the basis weight of one of the lobes 62a may be varied with that of the other lobe 62b in one end or both ends of the product.

The stabilizing member's main function is to provide the proper amount of flexibility to give the product sufficient rigidity to maintain good fit to the wearer's body while not unduly bunching up and deforming in the Z-direction 99 (the direction perpendicular to the X-Y plane of the product) when subjected to lateral compression forces. It is also possible to have this stabilizing member 60 perform other functions relative to the overall product design and functionality such as fluid distribution laterally and longitudinally along the product, fluid transfer to adjacent layers above or below the member, and fluid retention to protect against leakage. As a result, the stabilizing member 60 may take on certain fluid handling properties of the optional transfer layer 30 and the absorbent core 50. In any event, it is desirable that the stabilizing member 60 be designed to be fluid permeable so as to be able to pass fluids such as urine, menses or feces from the body or first side 92 down into the absorbent article 10.

Due to the fact that the stabilizing member 60 will have at least some degree of functionality relative to the fluid handling properties of the product, it is desirable that the lobes 62 and the resultant void areas 64 not extend into the central portion 86 of the product. This lack of void area 64 in the central portion 86, attributable to the lobes 62 in either or both of the front end portion 82 and rear end portion 84, allows the central portion 86, which is typically located anatomically in the area relative to the wearer which encounters the most direct insult of body exudates, maximize its fluid handling capabilities.

Suitable materials for the stabilizing member 60 include but are not limited to fibrous nonwoven web materials including staple fiber length nonwovens such as bonded carded webs including through air bonded carded webs (TABCW) and chemically bonded webs and more continuous fiber webs such as spunbond webs and meltblown webs as well at laminate materials formed from such webs and other materials. Furthermore, porous film layers can also be employed as part of the stabilizing member 60. It is desirable that at least a portion of said fibers in the stabilizing member 60 be bonded to one another by any conventional means such as heat and/or pressure bonding, ultrasonic bonding, chemical bonding, binders, adhesives, needling, hydroentangling or combinations of the foregoing. In addition, binder fibers with lower melting point portions such as bicomponent fibers may be used to achieve inter-fiber bonding of the nonwoven web. Foam materials such as open-cell or reticulated foams and closed-cell foams are suitable either alone or in combination with other materials to form the stabilizing member 60. In addition any or all of the foregoing materials may be subjected to further combining and processing such as by aperturing, lamination and embossing. For example, as with other layers of the product, the stabilizing member 60 may have one or more embossed area 24. Such embossments may be present in the central portion 86, the front end portion 88 or the rear end portion 90 as well as in any combination of the foregoing portions. Such embossments typically function as channels to receive and direct body fluids to other portions of the product for further fluid handling. Other embossments such as point embossments can serve to further bind the fibers together thereby giving the layer sufficient interfiber bond strength and integrity. Referring to FIG. 1, there can be seen a racetrack-type embossment 24a which generally parallels the contour of the main structure of the product and thereby covers a number of layers of the product. This embossment 24a also extends over the front end portion 82, the rear end portion 84 and the central portion 86 of the stabilizing member 60. It extends into and over the void area 64 between the lobes 62 adjacent the distal ends 70 of the lobes 62. Referring again to FIG. 1, there is shown another embossment 24b which is generally arcuate in shape. It extends into and over the void area 64 between the lobes 62 adjacent the proximal ends 68 of the lobes 62. These embossments can be contained in and extend vertically through any or all of the layers of the product and can be made, for example, using heat and/or pressure and/or ultrasonics and, if desired, supplemented with adhesives to retain the integrity of the embossments, especially when the product has been wetted.

One particularly suitable material for the stabilizing member 60 is a chemically bonded carded web. Such webs and their formation are readily available and known to those of ordinary skill in the art of fibrous nonwoven webs and personal care absorbent articles. One such chemically bonded carded web is available from the Korea Vilene Company, LTD, located in Kyunggi-do, Korea and available under the designation CB-070ADL. This web has a basis weight of 70 gsm and is composed of 70% by weight hollow PET fibers designated HCF and sold by the aforementioned Huvis Company, LTD, and 30% by weight ethylene vinyl acetate (EVA) binder material which is available in an emulsion under the designation Vinnapas 192 from Wacker Chemical Korea of Seoul, Korea. This chemically bonded carded web as with the other fibrous nonwoven webs described in connection with the present invention may be colored by using pigments in the fiber polymer blends or by printing colors onto a surface of the webs using, for example, gravure, inkjet or flexographic printing techniques.

Another suitable material for the stabilizing member is a bonded carded web such as a through air bonded carded web (TABCW) wherein the fibers are bonded together using heat and/or pressure. Such webs are described above with respect to the body side layer 20 and the optional surge layer 30 and can include binder fibers such as bicomponent or multi-constituent fibers wherein one polymer has a lower melting point that the other polymers in the web and which can be melted to form bonds with the other fibers and components within the web. As an example, such bonded carded webs can use fibers having staple lengths of between about 25 and about 50 mm and more desirably between about 35 and about 40 mm. Fiber sizes may range from about 2 to about 10 denier and basis weights may range from about 40 to about 100 gsm. As will readily be appreciated, however, these ranges are illustrative only as other fiber sizes, basis weights, staple lengths and deniers may be used individually or in combination to fit a particular need and therefore are contemplated as being within the scope of the present invention and appended claims. It is also possible to use blends of fibers such as a mix of bicomponent fibers and conventional staple fibers such as PET fibers. In addition, the bicomponent fibers can be varied as to their constituent components such as polyethylene (PE) sheath/polypropylene (PP) core, PE sheath/PET core and PET sheath/PET core (different melting temperature) fibers. Further, such fibers may be, for example, concentric sheath/core, eccentric sheath/core, side-by-side and islands-in-the-sea configurations.

Another suitable material for the stabilizing member 60 is foam material. Representative absorbent foam materials are described in U.S. Pat. No. 6,627,670 B2 to Mork et al., U.S. Pat. No. 6,071,580 to Bland et al., U.S. Pat. No. 7,439,276 B2 to Strandburg et al., and in PCT Publication Nos. WO2008/036942A2 to Vansumeren et al., WO2007/011728A2 to Kim et al., WO2008/052122A1 to Menning, and WO2008/100842A1 to Stockton et al., each of which is incorporated herein by reference in its entirety and to the extent it does not conflict herewith.

Yet another example of a category of materials suitable for use as a stabilizing member 60 are airlaid web materials. One such material is an 80 gsm airlaid web material available from the Sambo Company, LTD located in Daegu, Korea. This particular material comprises a blend of 70 percent by weight pulp cellulose fibers from the Weyerhaeuser Company with headquarters in Federal Way, Wash., USA and available under the designation NB416 and 20 percent by weight 1.5 denier, 3 mm long bicomponent fibers having a sheath/core configuration with a polyethylene sheath and a polypropylene core. These fibers are available from FiberVisions Corporation with offices in Duluth, Ga., USA under the trade designation AL-Adhesion-C ES fibers. The remaining portion of the airlaid web is 20 percent by weight ethylene vinyl acetate (EVA) binder which is available in an emulsion under the designation Vinnapas® 192 from Wacker Chemical Korea of Seoul, Korea. Optionally, if desired, the airlaid material can be colored by either adding small amounts of pigment (typically less than 0.1 percent by weight) or by color printing the external surface of the airlaid using gravure or flexographic printing techniques.

Such absorbent polymeric foam materials have a hydrophilic, flexible, polymeric foam structure of interconnected open-cells. A feature that can be useful in defining such polymeric foams is the cell structure. Foam cells, and especially cells that are formed by polymerizing a monomer-containing oil phase that 5 surrounds relatively monomer-free water-phase droplets, will frequently be substantially spherical in shape. These spherical cells are connected to each other by openings, which are referred to hereafter as holes between cells. Both the size or "diameter" of such spherical cells and the diameter of the openings (holes) between the cells are commonly used for characterizing foams in general. Because the cells and holes between the cells in a given sample of polymeric foam will not necessarily be of approximately the same size, average cell and hole sizes (i.e., average cell and hole diameters) will often be specified.

Cell and hole sizes are parameters that can impact a number of important mechanical and performance features of the foams, including the fluid wicking properties of these foams, as well as the capillary pressure that is developed within the foam structure. A number of techniques are available for determining the average cell and hole sizes of foams. The most useful technique involves a simple measurement based on the scanning electron photomicrograph of a foam sample. The foams, useful as absorbents for aqueous fluids, will desirably have an average cell size of from about 20 to about 200 microns (μm), more desirably from about 30 to about 190 μm, and most desirably from about 80 to about 180 μm; and a number average hole size of from about 5 to about 45 μm, more desirably from about 8 to about 40 μm, and most desirably from about 20 to about 35 μm.

For example, U.S. Pat. No. 6,071,580 to Bland et al. describes an absorbent, extruded, open cell thermoplastic foam. The foam has an open cell content of about 50 percent or more and an average cell size of up to about 1.5 millimeters. The foam is capable of absorbing a liquid at about 50 percent or more of its theoretical volume capacity when absorbing a liquid. The foam desirably has an average equivalent pore size of about 5 micrometers or more. The foam desirably has a structure substantially of cell walls and cell struts. Also described is a method for absorbing a liquid employing the foam by elongation of the extrudate of the extrusion die, and a method of enhancing absorbency of an open cell foam by applying a surfactant to an exposed surface of the foam such that the surfactant remains at the surface and does not infiltrate a substantial distance into the foam.

Suitable foam materials can also include various types of foams, including, but not limited to, thermoplastic foams, high internal phase emulsion (HIPE) foams and inverse high internal phase emulsion (I-HIPE) foams, and other suitable polymeric foams, including, but not limited to, those disclosed in U.S. Pat. No. 7,053,131 to Ko et al., U.S. Pat. No. 7,358,282 to Krueger et al., and U.S. Pat. No. 5,692,939 to DesMarais et. al., and in U.S. Patent Application Publication No. US2006/0148917 to Radwanski et al., each of which is incorporated herein by reference in its entirety and to the extent it does not conflict herewith. One such example of a suitable foam material is a polyurethane foam with a negative Poisson ratio. Materials typically used as backsheet materials in conventional feminine pads can also be suitable. Examples of extensible backsheet materials are described in U.S. Pat. No. 5,611,790 to Osbom, I I I et al., which is incorporated herein in its entirety by reference thereto to the extent it does not conflict herewith. Further examples of suitable absorbent foam materials are described in U.S. Patent Application Publication No. US2006/0246272 to Zhang et al., which is incorporated herein in its entirety by reference thereto to the extent it does not conflict herewith.

As with the other stabilizing member materials, the foam material may be formed in the desired end shape or it may be formed as a blank and then stamped or cut to the desired shape.

The stabilizing member may be attached to adjacent layers by any means known in the art used in joining layers of such personal care absorbent articles together. Examples include, but are not limited to, adhesives, bonding and embossing using heat and/or pressure, ultrasonics, stitching, heat-bondable fibers and particles, hydroentangling and needle punching.

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

The invention claimed is:

1. An absorbent article comprising:
a front end portion having a front end, a rear end portion having a rear end and a central portion separating said front end portion and said rear end portion;
a liquid permeable body-side layer;
a garment-side layer;
an absorbent core positioned between said body-side layer and said garment-side layer of said article; and
a stabilizing member positioned between said body-side layer and said garment-side layer of said article;
said stabilizing member being made from a stabilizing material and including a pair of lobes located in at least one of said front end portion or said rear end portion of said article, said pair of lobes extending away from said central portion toward a respective front or rear end, said pair of lobes defining a void therebetween devoid of said stabilizing member material, said void between said pair of lobes being generally centered about a lengthwise centerline of said article, each of said lobes in said pair having a proximal end adjacent said central portion and a distal end separated by a mid-section, said distal ends of each of said lobes being separated by a distal distance, said proximal ends of each of said lobes being separated by a proximal distance and said mid-section of each of said lobes being separated by a mid-distance, said distal distance being greater than said proximal distance and said mid-distance being less than said proximal distance, said void defined by said pair of lobes not extending into said central portion of said article.

2. The absorbent article of claim 1 wherein said article has a pair of lobes located in both said front end portion and said rear end portion of said article.

3. The absorbent article of claim 1 wherein said article has at least one embossment which extends over at least a portion of said void defined by said stabilizing member.

4. The absorbent article of claim 1 wherein said lobes adjacent said proximal end of said lobes terminate in a shape which causes said void to be defined by a relative V-shape about said lengthwise centerline of said absorbent article with an open end of said V-shape pointing towards said central portion of said absorbent article.

5. The absorbent article of claim 1 wherein during use said article, when subjected to lateral compression forces of a wearer, tends to reduce vertical bunching in an area of said article containing said lobes.

6. The absorbent article of claim 1 wherein said absorbent core comprises a fibrous nonwoven web material including at least 80% by weight viscose rayon.

7. The absorbent article of claim 6 wherein said web material is a hydroentangled viscose rayon spunlace material.

8. The absorbent article of claim 1 wherein said stabilizing member comprises a foam material.

9. The absorbent article of claim 1 wherein said article is a sanitary napkin.

10. The absorbent article of claim 1 wherein said proximal distance is between about 10 and about 40 millimeters.

11. The absorbent article of claim 1 wherein said mid-distance is between about 1 and about 30 millimeters.

12. The absorbent article of claim 1 wherein said distal distance is between about 30 and about 70 millimeters.

13. The absorbent article of claim 1 wherein the length of said stabilizing member is between about 80 and about 120 percent of the length of said absorbent core.

14. The absorbent article of claim 1 wherein the width of said stabilizing member is between about 70 and about 140 percent of the width of said absorbent core.

15. The absorbent article of claim 1 wherein said stabilizing member has a basis weight between about 40 and about 120 grams per square meter.

16. The absorbent article of claim 1 wherein said stabilizing member defines a void area with a substantially rounded end adjacent said central region.

17. The absorbent article of claim 1 wherein said stabilizing member defines a void area with a substantially triangular end adjacent said central region.

18. The absorbent article of claim 1 wherein said stabilizing member defines a void area with a substantially diamond-shaped end adjacent said central region.

* * * * *